United States Patent
Nguyen et al.

(10) Patent No.: US 10,062,280 B2
(45) Date of Patent: Aug. 28, 2018

(54) TRAFFIC NEWS INTERFACE

(71) Applicant: INRIX INC., Kirkland, WA (US)

(72) Inventors: Vu Nguyen, Redmond, WA (US); Sergei Tuterov, Seattle, WA (US); Ka Wang Yee, Renton, WA (US)

(73) Assignee: INRIX INC., Kirkland, WA (US)

( * ) Notice: Subject to any disclaimer, the term of this patent is extended or adjusted under 35 U.S.C. 154(b) by 128 days.

(21) Appl. No.: 15/122,720

(22) PCT Filed: Mar. 2, 2015

(86) PCT No.: PCT/US2015/018310
§ 371 (c)(1),
(2) Date: Aug. 31, 2016

(87) PCT Pub. No.: WO2015/134386
PCT Pub. Date: Sep. 11, 2015

(65) Prior Publication Data
US 2017/0069205 A1     Mar. 9, 2017

Related U.S. Application Data

(60) Provisional application No. 61/946,962, filed on Mar. 3, 2014.

(51) Int. Cl.
*G08G 1/00* (2006.01)
*G08G 1/0967* (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC .............. G08G 1/0129; G08G 1/0141; G08G 1/096791; H04W 4/046
See application file for complete search history.

(56) References Cited

U.S. PATENT DOCUMENTS

2007/0118281 A1   5/2007 Adam et al.
2008/0084473 A1*  4/2008 Romanowich ... G08B 13/19671
                                                   348/135
(Continued)

OTHER PUBLICATIONS

EP Search Report cited in EP Application No. 15758337.8 dated Nov. 7, 2017, 7 pgs.
(Continued)

*Primary Examiner* — Daryl Pope
(74) *Attorney, Agent, or Firm* — Cooper Legal Group, LLC

(57) ABSTRACT

One or more techniques and/or systems are provided for providing a traffic news interface. For example, a traffic news provider component may query traffic camera data and/or traffic incident data to identify traffic cameras and/or traffic incidents along a route of a driver. The traffic cameras and/or the traffic incidents may be ranked based upon a safety metric, a travel time sensitivity metric, an alternative route selection metric, a driving behavior pattern, a driver mood, a distance of a traffic camera or traffic incident from a current user location, and/or other information used to determine how relevant information from the traffic camera and/or a traffic incident is to this particular driver. A subset of traffic cameras and/or traffic incidents may be selected for inclusion within a traffic news interface based upon camera relevancy rankings and/or incident relevancy rankings.

20 Claims, 9 Drawing Sheets

(51) Int. Cl.

| | | |
|---|---|---|
| *G06N 99/00* | (2010.01) | |
| *G08G 1/01* | (2006.01) | |
| *G08G 1/0968* | (2006.01) | |
| *B60W 30/14* | (2006.01) | |
| *G05D 1/00* | (2006.01) | |
| *G07C 5/00* | (2006.01) | |
| *G08G 1/0965* | (2006.01) | |
| *A61B 5/0205* | (2006.01) | |
| *A61B 5/0476* | (2006.01) | |
| *A61B 5/00* | (2006.01) | |
| *G01C 21/34* | (2006.01) | |
| *G05D 1/02* | (2006.01) | |
| *H04B 1/3822* | (2015.01) | |
| *H04L 29/08* | (2006.01) | |
| *B64C 39/02* | (2006.01) | |
| *G08G 1/097* | (2006.01) | |
| *H04B 7/185* | (2006.01) | |
| *G06F 17/30* | (2006.01) | |
| *G06Q 20/10* | (2012.01) | |
| *G06Q 30/02* | (2012.01) | |
| *G08G 1/07* | (2006.01) | |
| *H04W 4/00* | (2018.01) | |
| *H04W 12/08* | (2009.01) | |
| *H04M 15/00* | (2006.01) | |
| *G06Q 40/08* | (2012.01) | |
| *H04L 9/32* | (2006.01) | |
| *B60R 16/023* | (2006.01) | |
| *G07B 15/00* | (2011.01) | |
| *G08G 1/0962* | (2006.01) | |
| *H04W 4/04* | (2009.01) | |
| *H04W 4/48* | (2018.01) | |
| *H04W 4/50* | (2018.01) | |
| *A61B 5/024* | (2006.01) | |
| *A61B 5/053* | (2006.01) | |
| *G06Q 50/30* | (2012.01) | |
| *G08G 1/065* | (2006.01) | |

(52) U.S. Cl.
CPC ........ *A61B 5/4845* (2013.01); *B60R 16/0236* (2013.01); *B60W 30/143* (2013.01); *B64C 39/024* (2013.01); *G01C 21/3415* (2013.01); *G01C 21/3469* (2013.01); *G05D 1/0011* (2013.01); *G05D 1/0088* (2013.01); *G05D 1/021* (2013.01); *G06F 17/30241* (2013.01); *G06N 99/005* (2013.01); *G06Q 20/102* (2013.01); *G06Q 30/0283* (2013.01); *G06Q 40/08* (2013.01); *G07B 15/00* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/07* (2013.01); *G08G 1/097* (2013.01); *G08G 1/0962* (2013.01); *G08G 1/0965* (2013.01); *G08G 1/0967* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/001* (2013.01); *H04W 4/046* (2013.01); *H04W 12/08* (2013.01); *A61B 5/024* (2013.01); *A61B 5/0531* (2013.01); *B60W 2710/1044* (2013.01); *B60W 2710/18* (2013.01); *B60W 2720/10* (2013.01); *B64C 2201/123* (2013.01); *G06Q 50/30* (2013.01); *G06Q 2240/00* (2013.01); *G08G 1/065* (2013.01); *H04W 4/48* (2018.02); *H04W 4/50* (2018.02)

(56) References Cited

U.S. PATENT DOCUMENTS

| | | | |
|---|---|---|---|
| 2009/0265105 A1* | 10/2009 | Davis ..................... | G01C 21/20 701/300 |
| 2010/0250369 A1 | 9/2010 | Peterson et al. | |
| 2012/0089423 A1 | 4/2012 | Tamir et al. | |
| 2012/0274508 A1 | 11/2012 | Brown et al. | |
| 2013/0106618 A1 | 5/2013 | Wormald et al. | |

OTHER PUBLICATIONS

Corresponding International Application No. PCT/US2015/018310, International Search report and written opinion dated Jun. 16, 2015.

\* cited by examiner

TRAFFIC NEWS INTERFACE

CROSS-REFERENCE TO RELATED APPLICATIONS

This application claims priority to U.S. Provisional Patent Application No. 61/946,962 titled "DETERMINING HOV/HOT LANE TRAVEL TIMES", filed on Mar. 3, 2014, which is hereby incorporated by reference.

BACKGROUND

Many users utilize various devices to obtain route information. In an example, a user may utilize a smartphone to obtain walking directions to a nearby restaurant. In another example, a user may utilize a vehicle navigation device to obtain a map populated with driving directions to an amusement park. In a driving situation, a driver may want to view information that may affect an arrival time to a destination, such as traffic congestion and/or road incidents (e.g., construction and accidents). Such information may be represented pictorially on a map. However, the map may be visually overwhelming to the driver because the map may provide more information than what the driver needs for assessing the status of the commute, which may be exacerbated when too much information is displayed on a relatively smaller visual display space (e.g., the smartphone, the visual navigation device, etc.). Thus, the driver may become distracted and the relatively more relevant information may become lost in the noise of all the possible points of interest along the user's route.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for providing a traffic news interface are provided herein. A news traffic provider component may be configured to identify a route of a driver from a starting location to a destination location. A current driver location of the driver along the route may be identified. Traffic camera data may be queried to identify a set of traffic cameras located along the route between the current driver location and the destination location. Camera relevancy rankings may be assigned to the traffic cameras within the set of traffic cameras (e.g., a camera relevancy ranking may be assigned based upon how helpful a traffic camera is at relaying visual information regarding the safety, arrival time, ability to select an alternative route, and/or other relevant information for the driver). A subset of the traffic cameras may be selected from the set of traffic cameras based upon the camera relevancy rankings (e.g., a number of highest ranking traffic cameras may be determined for selection based upon available display space within a traffic news interface). The traffic news interface may be constructed and populated with a route interface of the route (e.g., a map and traffic flow information of the route) and one or more traffic camera interfaces configured to display video streams associated with the subset of traffic cameras.

In an example, traffic incident data may be queried to identify a set of traffic incident reports associated with locations along the route between the current driver location and the destination location. Incident relevancy rankings may be assigned to the traffic incident reports within the set of traffic incident reports (e.g., an incident relevancy ranking may be assigned based upon metrics regarding how much an incident affects the safety, arrival time, ability to select an alternative route, and/or other relevant information for the driver). A subset of the traffic incident reports may be selected from the set of incident reports based upon the incident relevancy rankings (e.g., a number of highest ranking incident reports may be determined for selection based upon available display space within the traffic news interface). The subset of traffic incident reports may be included within the traffic news interface. The traffic news interface may be displayed through a device associated with the driver (e.g., projected onto a windshield of a vehicle, displayed through a vehicle navigation device, displayed on a smartphone, etc.).

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
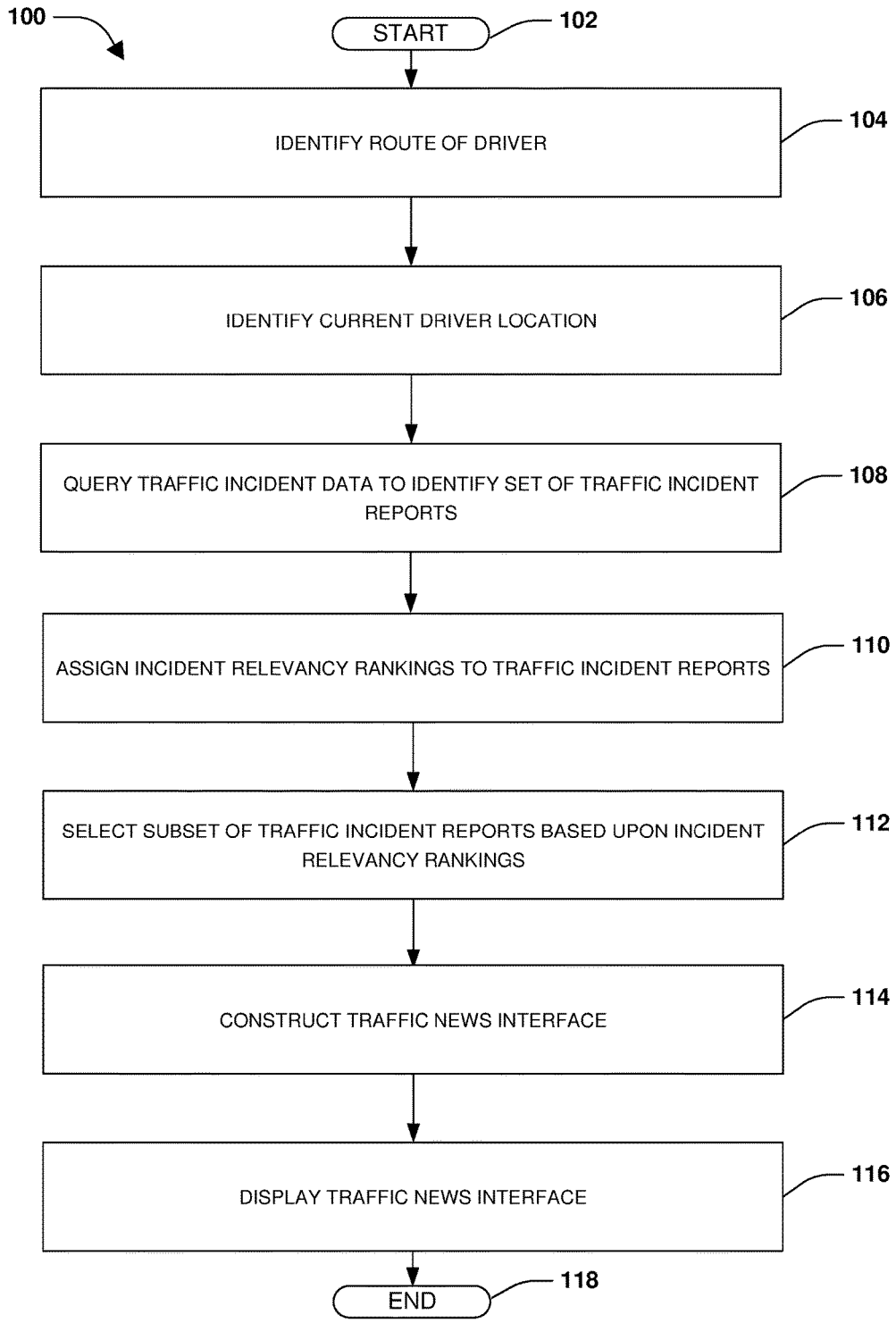
FIG. 1 is a flow diagram illustrating an exemplary method of providing a traffic news interface populated with traffic incident reports.

The claimed subject matter is now described with reference to the drawings, wherein like reference numerals are generally used to refer to like elements throughout. In the following description, for purposes of explanation, numerous specific details are set forth to provide an understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for providing a traffic news interface are provided herein. Many devices, such as mobile devices and vehicle navigation devices, may have limited visual display space. Populating a visual interface of such devices with all available points of interest (e.g., traffic incident reports, traffic camera video streams, accident indicators, traffic flow indicators, etc.) along a user's route may result in messy and/or unreadable displays of information. Displaying all of the available points of interest may result in the more relevant points of interest being lost in the noise. Accordingly, as provided herein, a traffic news interface may be selectively populated with subsets of traffic cameras and/or traffic incident reports that may be relatively more interesting and/or informative to a particular user, which may conserve visual display space so that the information is readable and the signal-to-noise ratio (e.g., the ability of the user to easily identify relevant information) may be improved. In this way, the presentation of traffic information may be improved by providing merely relevant information based upon signals about the user's current state and priorities (e.g., safety, time of arrival, avoiding trucks, traveling salted roads, avoiding busy roads regardless of traffic flow speed, using a fastest route regardless of traffic density or accidents, etc.).

An embodiment of providing a traffic news interface is illustrated by an exemplary method 100 of FIG. 1. At 102, the method 100 starts. At 104, a route of a driver from a starting location to a destination location may be identified (e.g., the driver may be taking her children to a children's art museum that is 15 miles away, which may be identified based upon the driver setting a navigation route to the children's art museum through a vehicle navigation device of a vehicle). At 106, a current driver location of the driver along the route may be identified (e.g., global positioning system (GPS) of the vehicle may be used to identify the current location as near an onramp to an expressway).

Various contextual information about the driver, driving preferences, and/or driving behavior of the driver may be obtained. In an example, the driver may indicate that children are in the car and thus the driver may prefer safety over speed and time of arrival. Such preferences may be used to identify a safety metric (e.g., safety may be a high priority) and a travel time sensitivity metric (e.g., travel time may be a low priority). In another example, prior driving habits of the driver may indicate that the driver prefers to take alternative routes to avoid unsafe driving conditions. Such preferences may be used to identify an alternative route selection metric (e.g., safer alternative routes may be a high priority). In another example, vehicle telemetry of the vehicle may be evaluated to determine a driving behavior pattern of the driver (e.g., sensors may provide braking patterns, acceleration/deceleration patterns, lane changing patterns, etc.). In another example, social network data (e.g., the driver may indicate that she hopes they have a safe trip to the children's art museum), gaze tracking information (e.g., a camera of the vehicle navigation device may be used to determine that the driver seems distracted by the children passengers), and/or driver feedback (e.g., the driver may speak to the vehicle navigation device that the driver is not in the mood to drive through areas with crime or accidents) may be evaluated to identify a driver mood.

At 108, traffic incident data may be queried to identify a set of traffic incident reports associated with locations along the route between the current driver location and the destination location (e.g., a user may report a traffic incident to a social network; a traffic monitoring service may monitor traffic incidents; etc.). At 110, incident relevancy rankings may be assigned to traffic incident reports within the set of traffic incident reports. For example, the incident relevancy rankings may be assigned based upon the user safety metric, the travel time sensitivity metric, the alternative route selection metric, the driving behavior pattern, the driver mood, a distance of a traffic incident from the current user location, and/or a variety of other metrics used to indicate how relevant a traffic incident may be to the particular driver.

At 112, a subset of the traffic incident reports may be selected from the set of traffic incident reports based upon the incident relevancy rankings. In an example, a number of traffic incident reports to select may be based upon available visual display space of the vehicle navigation device, and thus the number of highest ranking traffic incident reports may be selected. In another example, traffic incident reports having incident relevancy rankings above a relevancy threshold may be selected. At 114, a traffic news interface, populated with the subset of traffic incident reports, may be constructed. In an example, the traffic incident reports may be populated within an interface, such as a scroll interface (e.g., a vertical scroll interface), of the traffic news interface. In an example, a traffic incident report may be associated with a traffic incident report interface that may be populated with a delay for the driver based upon the traffic incident (e.g., a 15 minute delay), a backup length caused by the traffic incident (e.g., a 2 mile back of cars), a user that reported the traffic incident, and/or a description of the traffic incident.

In an example, the traffic news interface may be populated with a route interface of the route. For example, traffic condition data may be queried to identify a current traffic condition for the route (e.g., accident data, traffic flow speeds, construction, etc.). A map provider may be queried to obtain a map of the route. The map may be populated with the route based upon the current traffic condition (e.g., road segments may be colored, highlighted, and/or visually modified based upon traffic flow; an accident icon may be displayed for an accident; etc.). The map may be included within the traffic news interface, such as within the route interface.

In an example, traffic camera data may be queried to identify a set of traffic cameras located along the route between the current driver location and the destination location. Camera relevancy rankings may be assigned to traffic cameras within the set of traffic cameras. For example, the camera relevancy rankings may be assigned based upon the user safety metric, the travel time sensitivity metric, the alternative route selection metric, the driving behavior pattern, the driver mood, a distance of a traffic camera from the current user location, and/or a variety of other metrics used to indicate how relevant a traffic camera may be to the particular driver. A subset of the traffic cameras may be selected from the set of traffic cameras based upon the camera relevancy rankings. In an example, a number of traffic cameras to select may be based upon available visual display space of the vehicle navigation device, and thus the number of highest ranking traffic cameras may be selected. In another example, traffic cameras having camera relevancy rankings above a relevancy threshold may be selected. The traffic news interface may be populated with one or more traffic camera interfaces configured to display video streams associated with the subset of traffic cameras. In an example, the traffic camera interfaces may be populated within an interface, such as a scroll interface (e.g., a horizontal scroll interface), of the traffic news interface.

In an example, the subset of traffic incident reports and/or traffic condition data (e.g., traffic flow information, delay information, etc.) for the route may be evaluated to identify an alternative route (e.g., a safer route, a faster route, etc.). The alternative route may be populated within the traffic news interface. At 216, the traffic news interface may be displayed through a device associated with the driver. In an example, the traffic news interface may be displayed through the vehicle navigation device. In another example, the traffic news interface may be projected onto a dashboard or windshield of the vehicle.

In an example, a new traffic incident may be identified (e.g., a user may report a new incident along the route). An impact of the new traffic incident on a commute of the driver along the route may be determined (e.g., a safety impact and/or time of arrival impact of an iced over bridge). Responsive to the impact of the new traffic incident exceeding a threshold, a push notification of the new traffic incident may be provided to the device.

In an example, a new driver location of the driver may be identified (e.g., the driver may have traveled a quarter of a mile along the route). The traffic incident data and/or the traffic camera data may be queried to identify an updated set of traffic incident data and/or an updated set of traffic cameras based upon the new driver location. New incident relevancy rankings may be assigned to the traffic incident reports within the updated set of traffic incident reports, and new camera relevancy rankings may be assigned to traffic cameras within the updated set of traffic cameras. An updated subset of traffic cameras and/or an updated subset of traffic incident reports may be selected based upon the new camera relevancy rankings and/or the new incident relevancy rankings. The updated subset of traffic cameras and/or the updated subset of traffic incident reports may be provided through the traffic news interface. At 118, the method 100 ends.

Figure 2:
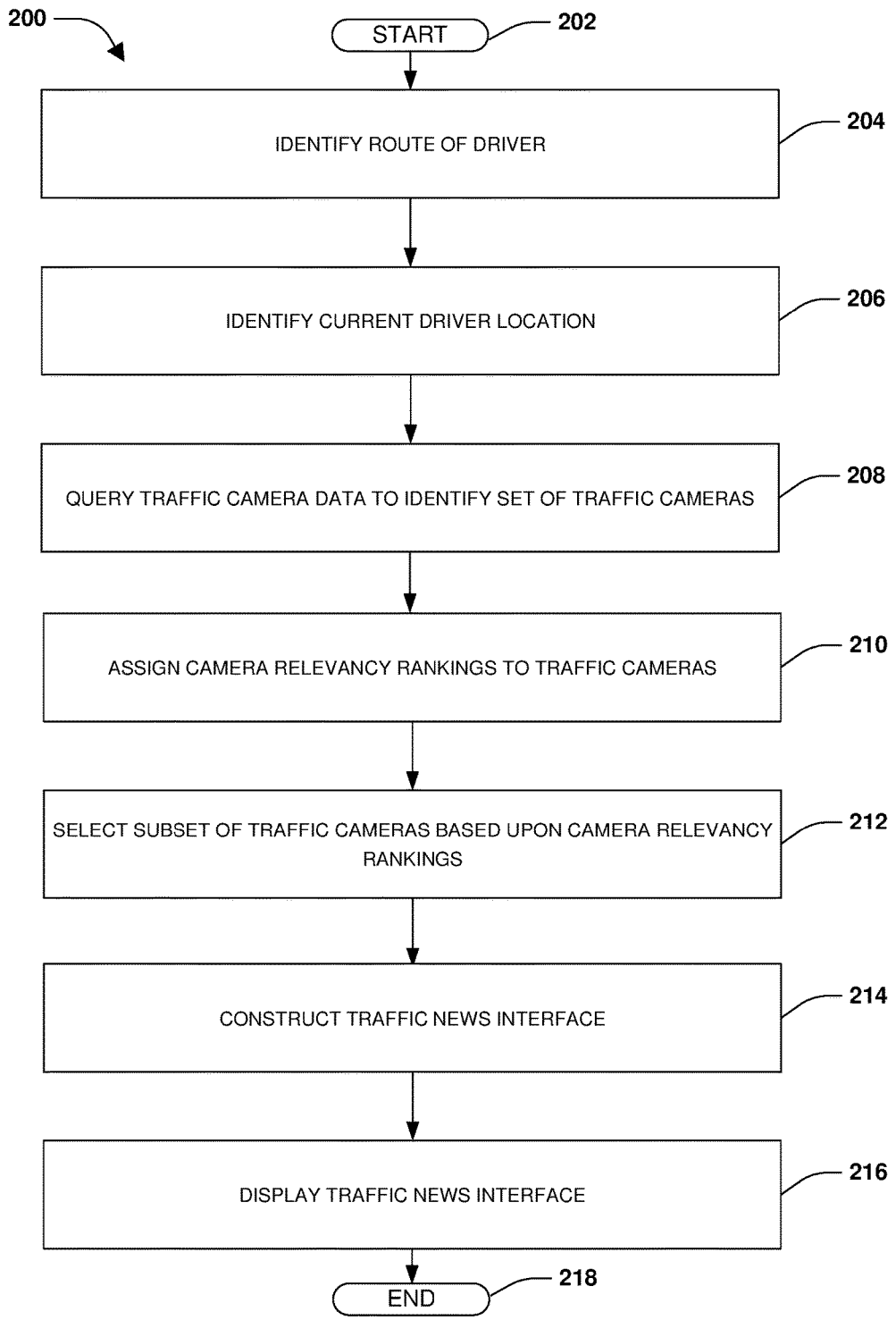
FIG. 2 is a flow diagram illustrating an exemplary method of providing a traffic news interface populated with traffic camera interfaces.

An embodiment of providing a traffic news interface is illustrated by an exemplary method 200 of FIG. 2. At 202, the method 200 starts. At 204, a route of a driver from a starting location to a destination location may be identified. At 206, a current driver location of the driver along the route may be identified. At 208, traffic camera data may be queried to identify a set of traffic cameras located along the route between the current driver location and the destination location. At 210, camera relevancy rankings may be assigned to traffic cameras within the set of traffic cameras. At 212, a subset of traffic cameras may be selected from the set of traffic cameras based upon the camera relevancy rankings. At 214, a traffic news interface, populated with a route interface of the route and one or more traffic camera interfaces configured to display video streams associated with the subset of traffic cameras, may be constructed. At 216, the traffic news interface may be displayed through a device associated with the driver. At 218, the method 200 ends.

Figure 3A:
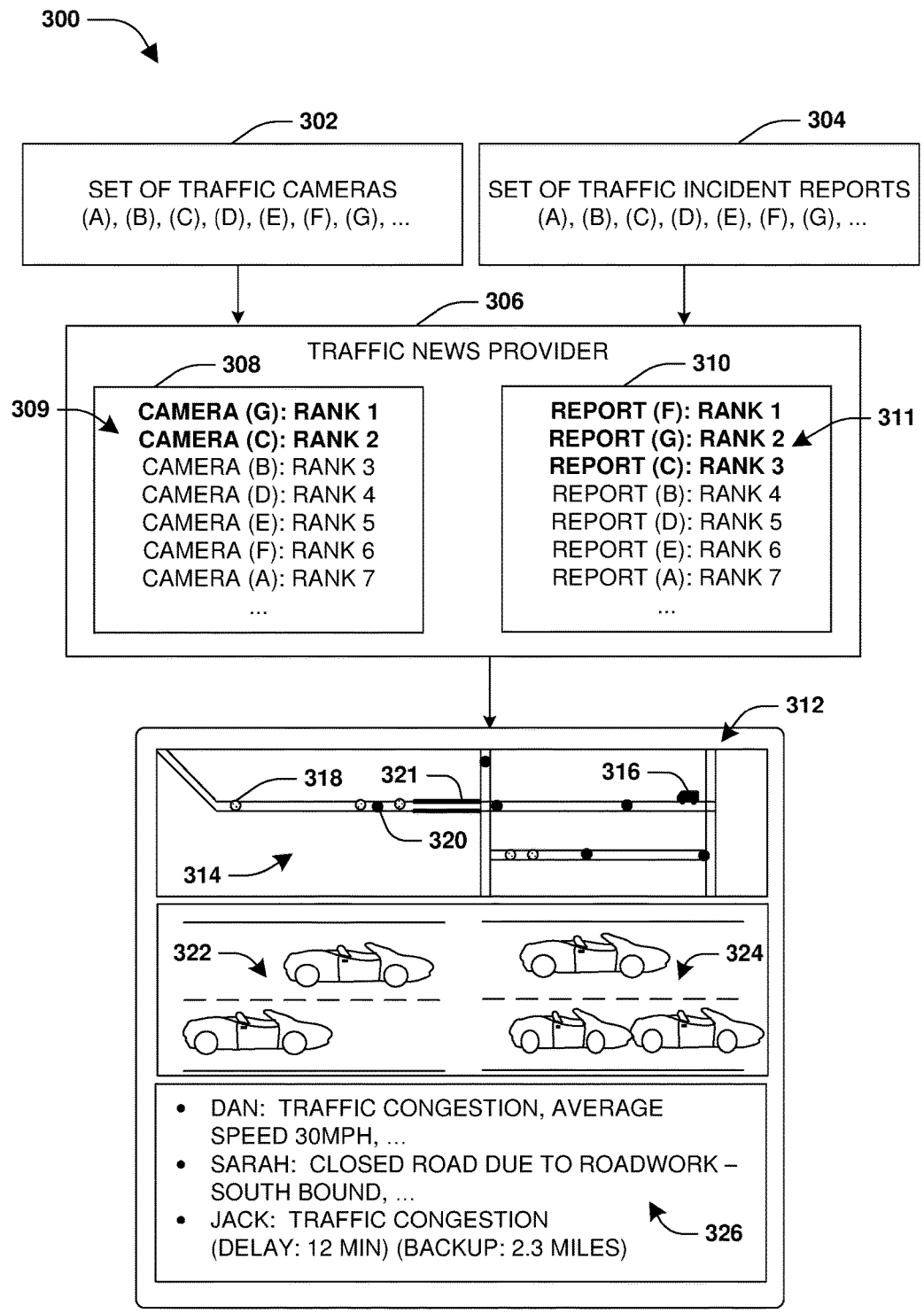
FIG. 3A is a component block diagram illustrating an exemplary system for providing a traffic news interface.
Figure 3B:
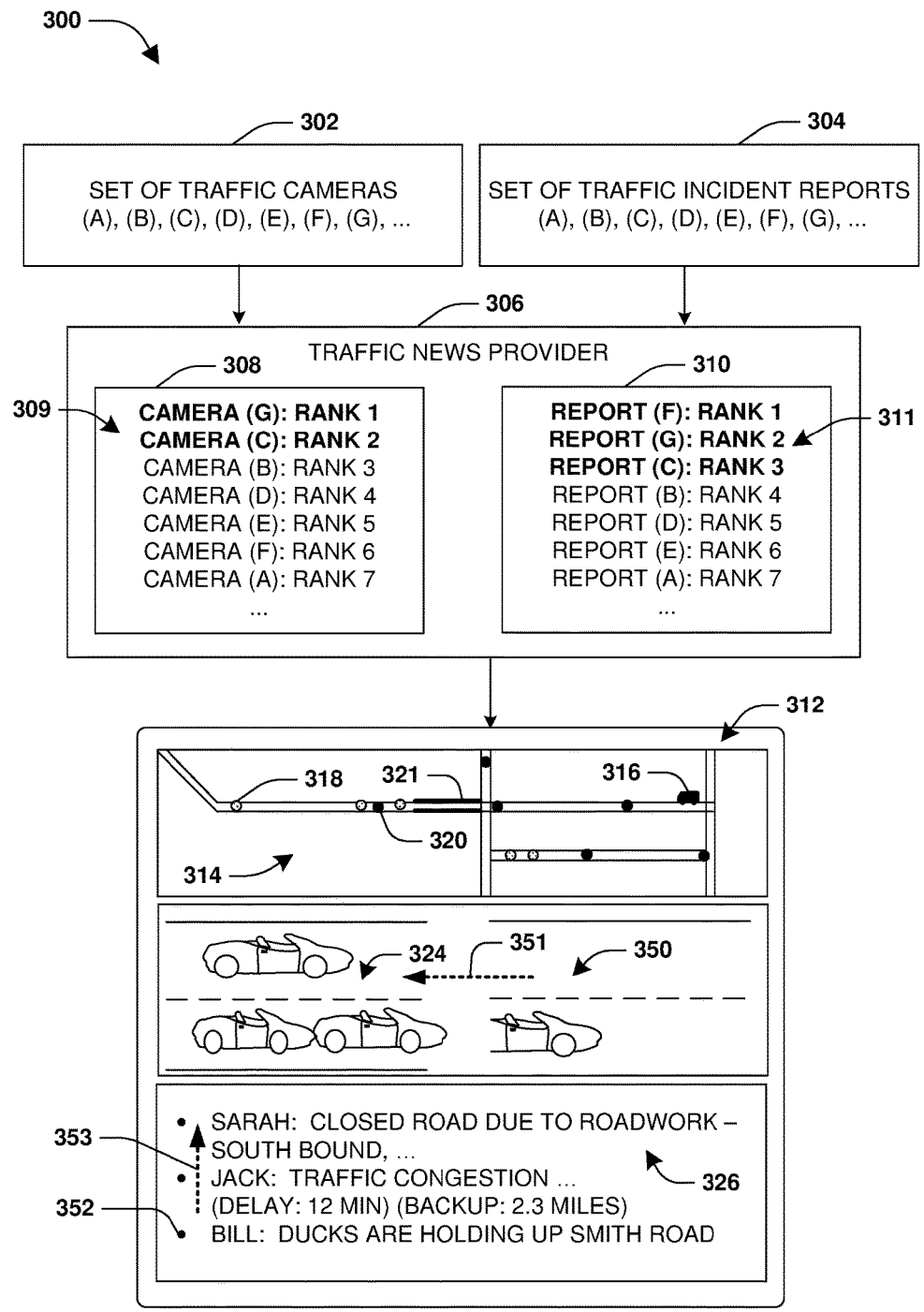
FIG. 3B is a component block diagram illustrating an exemplary system for providing a traffic news interface, where a driver scrolls between traffic camera interfaces and/or traffic incident reports.
Figure 3C:
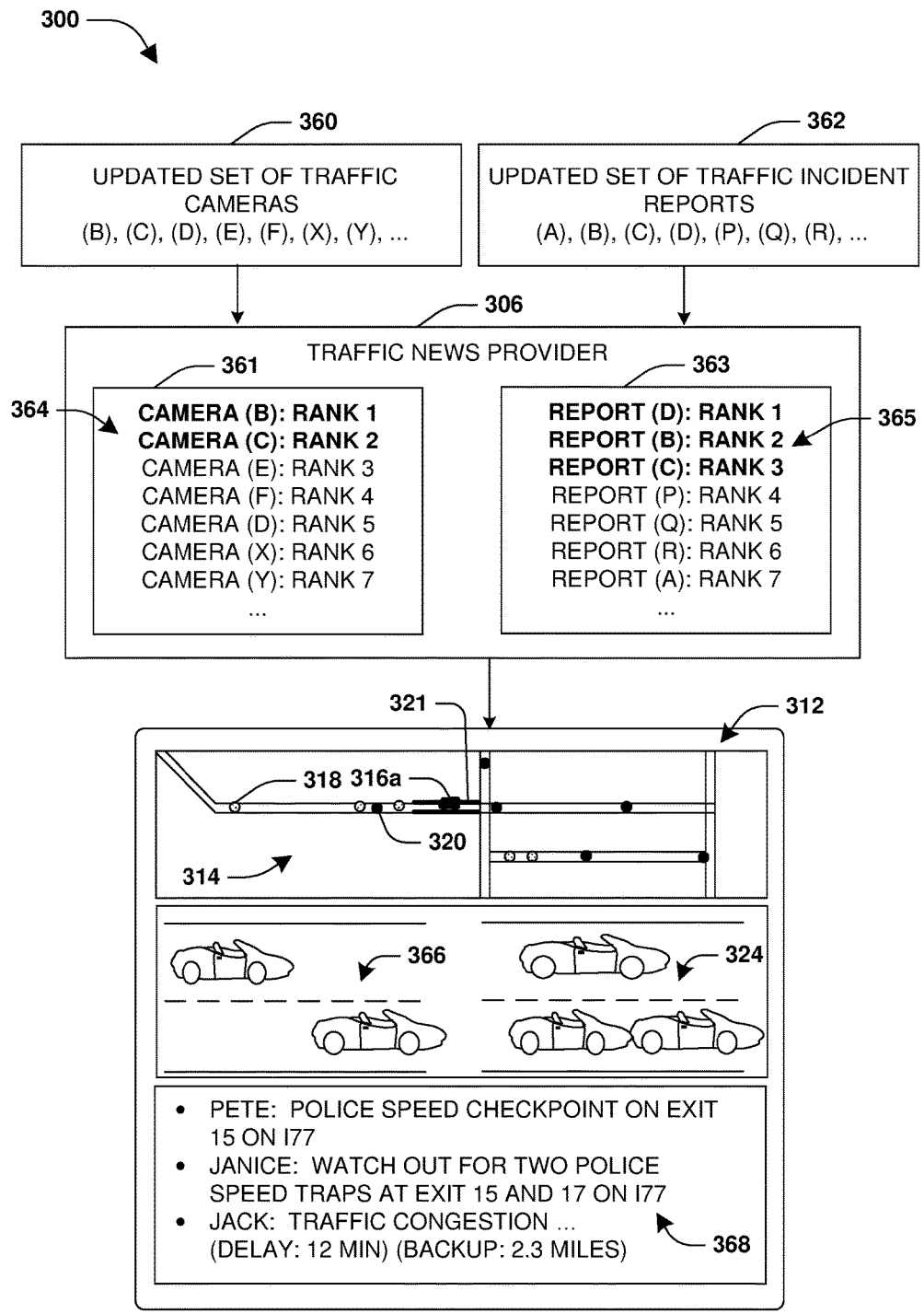
FIG. 3C is a component block diagram illustrating an exemplary system for providing a traffic news interface, where the traffic news interface is updated with information based upon a new driver location.

FIGS. 3A-3C illustrate examples of a system 300, comprising a traffic news provider component 306, configured to provide a traffic news interface 312. FIG. 3A illustrates the traffic news provider component 306 identifying a route of a driver from a starting location to a destination location (e.g., the driver may specify through a driving app on a smartphone that the driver wants driving directions to a work conference). The traffic news provider component 306 may identify a current driver location 316 of the driver along the route (e.g., the driver may be driving through a neighborhood towards an expressway).

The traffic news provider component 306 may query traffic camera data to identify a set of traffic cameras 302 located along the route between the current driver location 316 and the destination location. For example, the set of traffic cameras 302 may comprise a traffic camera (A), a traffic camera (B), a traffic camera (C), a traffic camera (D), a traffic camera (E), a traffic camera (F), a traffic camera (G), and/or other traffic cameras. The traffic news provider component 306 may assign camera relevancy rankings to traffic cameras within the set of traffic cameras 302 to create a ranked set of traffic cameras 308 (e.g., traffic cameras depicting portions of the route that may have an impact on a commute time of the driver may be ranked higher than other traffic cameras depicting normal traffic flow and conditions with less of an impact on the commute time). A subset of traffic cameras 309, such as the traffic camera (G) and the traffic camera (C) having the highest camera relevancy rankings, may be selected from the ranked set of traffic cameras 308. The traffic news provider component 306 may populate the traffic news interface 312 with a first traffic camera interface 322 configured to display video streams associated with the traffic camera (G). The traffic news provider component 306 may populate the traffic news interface 312 with a second traffic camera interface 324 configured to display video streams associated with the traffic camera (C).

The traffic news provider component 306 may query traffic incident data to identify a set of traffic incident reports 304 associated with locations along the route between the current driver location 316 and the destination location. For example, the set of traffic incident reports 304 may comprise a traffic incident report (A), a traffic incident report (B), a traffic incident report (C), a traffic incident report (D), a traffic incident report (E), a traffic incident report (F), a traffic incident report (G), and/or other traffic incident reports. The traffic news provider component 306 may assign incident relevancy rankings to traffic incident reports within the set of traffic incident reports 304 to create a ranked set of traffic incident reports 310 (e.g., traffic incident reports describing traffic incidents that may have an impact on the commute time of the driver may be ranked higher than other traffic incident reports that may have less of an impact on the commute time). A subset of traffic incident reports 311, such as the traffic incident report (F), the traffic incident report (G), and the traffic incident report (C) having highest incident relevancy rankings, may be selected from the ranked set of traffic incident reports 310. The traffic news provider component 306 may populate an incident report interface 326 of the traffic news interface 312 with the traffic incident report (F) (e.g., user Dan may have reported traffic congestion with an average speed of 30 mph), the traffic incident report (G) (e.g., user Sarah may have reported a road closure due to southbound roadwork on a particular road), and the traffic incident report (C) (e.g., user Jack may have reported traffic congestion). In an example, a delay of 12 minutes and a 2.3 mile backup may be identified and displayed with the traffic incident report (C).

The traffic news provider component 306 may query traffic condition data to identify a current traffic condition for the route (e.g., a slow traffic flow portion 321 near an onramp to the expressway). The traffic news provider component 306 may query a map provider to obtain a map 314 of the route. The traffic news provider component 306 may populate the map 314 with the route based upon the current traffic condition (e.g., the slow traffic flow portion 321 may be highlighted with a red color). The traffic news provider component 306 may populate the route with a user icon representing the current driver location 316, a camera icon 320 representing an available traffic camera, a traffic incident report icon 318 representing a traffic incident report location, and/or other information.

FIG. 3B illustrates the driver horizontally scrolling 351 through traffic camera interfaces and vertically scrolling 353 through traffic incident reports. For example, responsive to the horizontal scrolling 351 through traffic camera interfaces, the first traffic camera interface 322, displaying video streams associated with the traffic camera (G), may be scrolled out of view. The second traffic camera interface 324, displaying video streams associated with the traffic camera (C), may be scrolled to the left of the screen. The traffic news provider component 306 may evaluate the ranked set of traffic cameras 308 to identify a next highest ranked traffic camera, such as the traffic camera (B), to display through a third traffic camera interface 350. The traffic news provider component 306 may populate the traffic news interface 312 with the third traffic camera interface 350, configured to display video streams associated with the traffic camera (B), based upon the horizontal scrolling 351.

Responsive to the vertical scrolling 353 through the traffic incident reports, the traffic incident report (F) may be scrolled out of view and the traffic incident report (G) and the traffic incident report (C) may be scrolled up. The traffic news provider component 306 may evaluate the ranked set of incident reports 310 to identify a next highest ranked traffic incident report, such as the traffic incident report (B). The traffic news provider component 306 may display 352 the traffic incident report (B) through the traffic news interface 312 based upon the vertical scrolling 353.

FIG. 3C illustrates the traffic news provider component 306 identifying a new driver location 316a of the driver. The traffic news provider component 306 may query the traffic camera data to identify an updated set of traffic cameras 360 along the route between the new driver location 316a and the destination location. For example, the updated set of traffic cameras 360 may comprise the traffic camera (B), the traffic camera (C), the traffic camera (D), the traffic camera (E), the traffic camera (F), a traffic camera (X), a traffic camera (Y), and/or other traffic cameras. The traffic news provider component 306 may assign new camera relevancy rankings to traffic cameras within the updated set of traffic cameras 360 to create a new ranked set of traffic cameras 361. An updated subset of traffic cameras 364, such as the traffic camera (B) and the traffic camera (C) having the highest camera relevancy rankings, may be selected from the updated ranked set of traffic cameras 361. The traffic news provider component 306 may populate the traffic news interface 312 with a third traffic interface 366 configured to display video streams associated with the traffic camera (B). The traffic news provider component 306 may populate the traffic news interface 312 with the second traffic camera interface 324 configured to display video streams associated with the traffic camera (C).

The traffic news provider component 306 may query the traffic incident data to identify an updated set of traffic incident reports 362 along the route between the new driver location 316a and the destination location. For example, the updated set of traffic incident reports 362 may comprise the traffic incident report (A), the traffic incident report (B), the traffic incident report (C), the traffic incident report (D), a traffic incident report (P), a traffic incident report (Q), a traffic incident report (R), and/or other traffic incident reports. The traffic news provider component 306 may assign new incident relevancy rankings to traffic incident reports within the updated set of traffic incident reports 362 to create a new ranked set of traffic incident reports 363. An updated subset of traffic incident reports 365, such as the traffic incident report (D), the traffic incident report (B), and the traffic incident report (C) having the highest incident relevancy rankings, may be selected from the updated ranked set of traffic incident reports 363. The traffic news provider component 306 may populate the traffic news interface 312 with an updated incident report interface 368 comprising the traffic incident report (D), the traffic incident report (B), and the traffic incident report (C).

Figure 4:
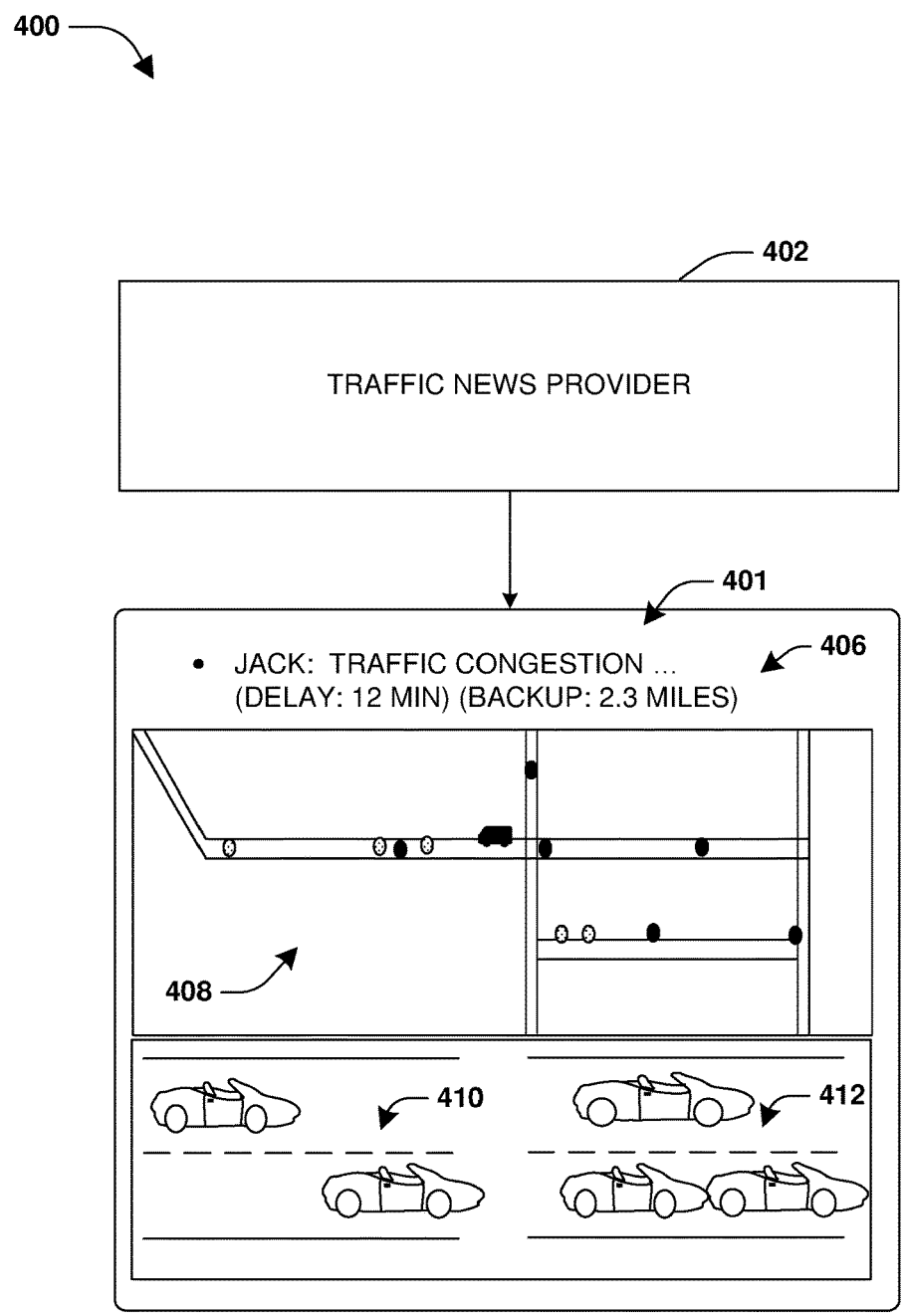
FIG. 4 is a component block diagram illustrating an exemplary system for providing a traffic news interface.

FIG. 4 illustrates an example of a system 400, comprising a traffic news provider component 402, for displaying a traffic news interface 401 to a driver. The traffic news provider component 402 may construct the traffic news interface 401. The traffic news provider component 402 may populate the traffic news interface 401 with a traffic incident report 406 based upon the traffic incident report having an incident relevancy ranking above a threshold, such as being a highest ranked traffic incident report based upon a safety metric (e.g., how important a safe driving route is to the driver, and thus how informative is the traffic incident report to the driver regarding safety), a travel time sensitivity metric (e.g., how important an arrival time is to the driver, and thus how informative is the traffic incident report to the driver regarding an impact on the driver's arrival time), an alternative route selection metric (e.g., how important is having an opportunity to take an alternative route such as a safer or faster route to the driver, and thus how informative is the traffic incident report to the driver regarding the driver's ability to select an alternative route), a distance of a traffic incident from a current location of the driver, a driver mood (e.g., social network data, gaze tracking information, and/or driver feedback such as driver behavior and statements of the driver may be indicators of the driver mood, such as an anxious mood about being late, and thus the traffic incident report may be ranked based upon how informative the traffic incident report is to the driver regarding the driver's ability to identify a fastest route), driving behavior pattern of the driver (e.g., braking patterns and/or other vehicle telemetry may indicate that the driver is tailgating other drivers, and thus a traffic incident that may require sudden stops may be relatively important to alert the driver about), and/or other information used to rank traffic incident reports.

The traffic news provider component 402 may populate the traffic news interface 401 with a map 408 comprising a route of the driver, traffic conditions of the route, available traffic cameras to view, and/or available traffic incident reports to view. The traffic news provider component 402 may populate the traffic news interface 401 with a first traffic camera interface 410 and a second traffic camera interface 412 that are configured to display video streams associated with a first traffic camera and a second traffic camera, such as traffic cameras having highest camera relevancy rankings based upon the safety metric, the travel time sensitivity metric, the alternative route selection metric, a distance of a traffic camera from a current location of the driver, the driver mood, the driving behavior pattern of the driver, and/or other information used to rank traffic cameras. The traffic news provider component 402 may display the traffic news interface 401 to the driver.

Figure 5:
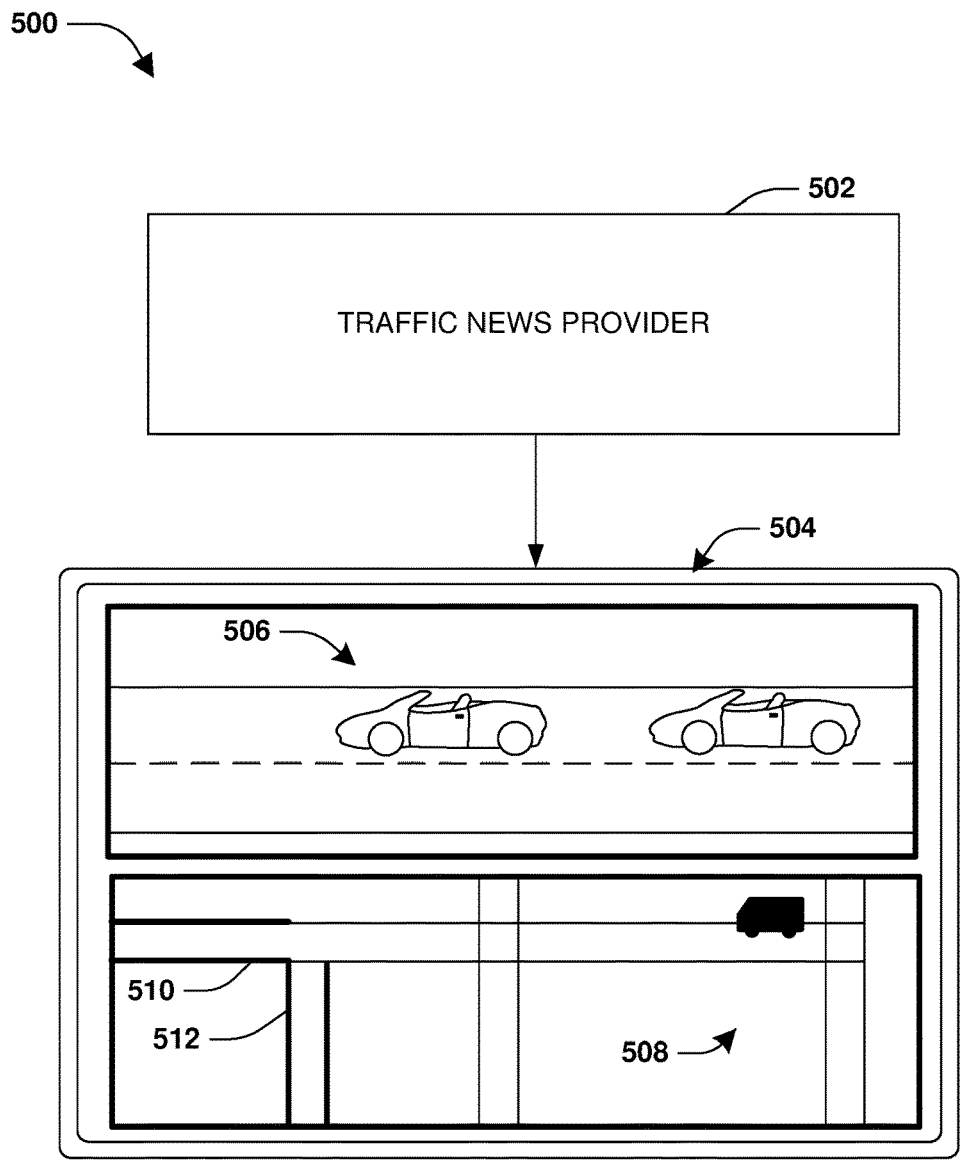
FIG. 5 is a component block diagram illustrating an exemplary system for providing a traffic news interface.

FIG. 5 illustrates an example of a system 500, comprising a traffic news provider component 502, for displaying a traffic news interface 504 to a driver. The traffic news provider component 502 may construct the traffic news interface 504. The traffic news provider component 502 may populate the traffic news interface 504 with a traffic camera interface 506 configured to display video streams associated with a traffic camera having a camera relevancy ranking above a threshold, such as being an highest ranked traffic camera based upon a safety metric (e.g., how important a safe driving route is to the driver, and thus how informative the traffic camera is to the driver regarding safety), a travel time sensitivity metric (e.g., how important an arrival time is to the driver, and thus how informative the traffic camera is to the driver regarding an impact on the driver's arrival time), an alternative route selection metric (e.g., how important is having an opportunity to take an alternative route such as a safer or faster route to the driver, and thus how informative is the traffic camera to the driver regarding the driver's ability to select an alternative route), a distance of the traffic camera from a current location of the driver, a driver mood (e.g., social network data, gaze tracking information, and/or driver feedback such as driver behavior and statements of the driver may be indicators of the driver mood, such as an anxious mood from being late, and thus the traffic camera may be ranked based upon how informative the traffic camera is to the driver regarding the driver's ability to identify a fastest route), driving behavior pattern of the driver (e.g., braking patterns and/or other vehicle telemetry may indicate that the driver is tailgating other drivers, and thus a traffic camera illustrating traffic flow that may require sudden stops may be relatively important to alert the driver about), and/or other information used to rank traffic cameras.

The traffic news provider component 502 may populate the traffic news interface 504 with a map 508 comprising a route of the driver, traffic conditions of the route, available traffic cameras to view, and/or available traffic incident reports to view. For example, a visual property of a first road segment 510 and a second road segment 512 may be modified to indicate a relatively slow traffic flow for such segments (e.g., a change in color, a change in line thickness, etc.). The traffic news provider component 502 may display the traffic news interface 504 to the driver.

Figure 6:
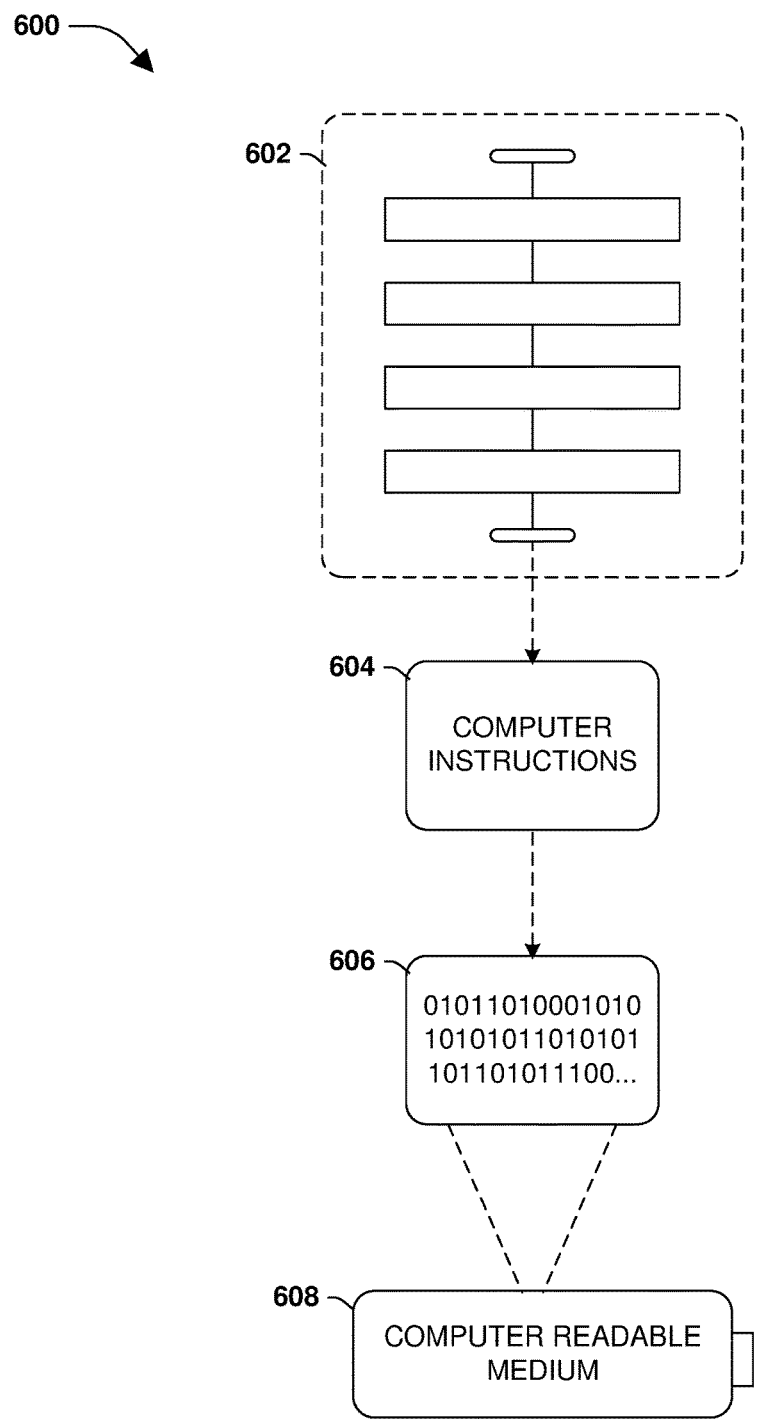
FIG. 6 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 6, wherein the implementation 600 comprises a computer-readable medium 608, such as a CD-R, DVD-R, flash drive, a platter of a hard disk drive, etc., on which is encoded computer-readable data 606. This computer-readable data 606, such as binary data comprising at least one of a zero or a one, in turn comprises a set of computer instructions 604 configured to operate according to one or more of the principles set forth herein. In some embodiments, the set of computer instructions 604 are configured to perform a method 602, such as at least some of the exemplary method 100 of FIG. 1 and/or at least some of the exemplary method 200 of FIG. 2, for example. In some embodiments, the set of computer instructions 604 are configured to implement a system, such as at least some of the exemplary system 300 of FIGS. 3A-3C, at least some of the exemplary system 400 of FIG. 4, and/or at least some of the exemplary system 500 of FIG. 5, for example. Many such computer-readable media are devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 7:
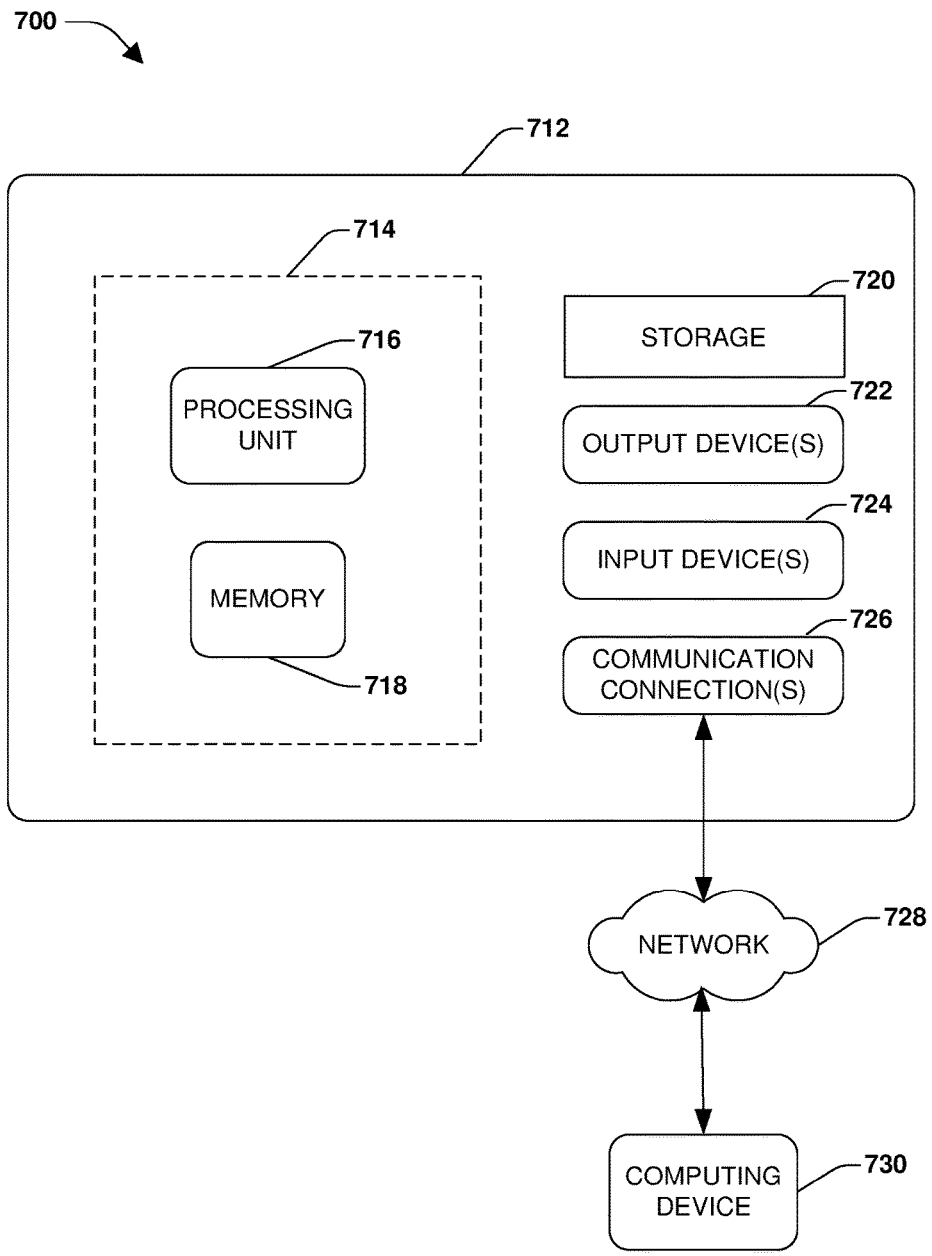
FIG. 7 illustrates an exemplary computing environment wherein one or more of the provisions set forth herein may be implemented.

FIG. 7 and the following discussion provide a brief, general description of a suitable computing environment to implement embodiments of one or more of the provisions set forth herein. The operating environment of FIG. 7 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 7 illustrates an example of a system 700 comprising a computing device 712 configured to implement one or more embodiments provided herein. In one configuration, computing device 712 includes at least one processing unit 716 and memory 718. Depending on the exact configuration and type of computing device, memory 718 may be volatile (such as RAM, for example), non-volatile (such as ROM, flash memory, etc., for example) or some combination of the two. This configuration is illustrated in FIG. 7 by dashed line 714.

In other embodiments, device 712 may include additional features and/or functionality. For example, device 712 may also include additional storage (e.g., removable and/or non-removable) including, but not limited to, magnetic storage, optical storage, and the like. Such additional storage is illustrated in FIG. 7 by storage 720. In one embodiment, computer readable instructions to implement one or more embodiments provided herein may be in storage 720. Storage 720 may also store other computer readable instructions to implement an operating system, an application program, and the like. Computer readable instructions may be loaded in memory 718 for execution by processing unit 716, for example.

The term "computer readable media" as used herein includes computer storage media. Computer storage media includes volatile and nonvolatile, removable and non-removable media implemented in any method or technology for storage of information such as computer readable instructions or other data. Memory 718 and storage 720 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 712. Computer storage media does not, however, include propagated signals. Rather, computer storage media excludes propagated signals. Any such computer storage media may be part of device 712.

Device 712 may also include communication connection(s) 726 that allows device 712 to communicate with other devices. Communication connection(s) 726 may include, but is not limited to, a modem, a Network Interface Card (NIC), an integrated network interface, a radio frequency transmitter/receiver, an infrared port, a USB connection, or other interfaces for connecting computing device 712 to other computing devices. Communication connection(s) 726 may include a wired connection or a wireless connection. Communication connection(s) 726 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 712 may include input device(s) 724 such as keyboard, mouse, pen, voice input device, touch input device, infrared cameras, video input devices, and/or any other input device. Output device(s) 722 such as one or more displays, speakers, printers, and/or any other output device may also be included in device 712. Input device(s) 724 and output device(s) 722 may be connected to device 712 via a wired connection, wireless connection, or any combination thereof. In one embodiment, an input device or an output device from another computing device may be used as input device(s) 724 or output device(s) 722 for computing device 712.

Components of computing device 712 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 712 may be interconnected by a network. For example, memory 718 may be comprised of multiple physical memory units located in different physical locations interconnected by a network.

Those skilled in the art will realize that storage devices utilized to store computer readable instructions may be distributed across a network. For example, a computing device 730 accessible via a network 728 may store computer readable instructions to implement one or more embodiments provided herein. Computing device 712 may access computing device 730 and download a part or all of the computer readable instructions for execution. Alternatively, computing device 712 may download pieces of the computer readable instructions, as needed, or some instructions may be executed at computing device 712 and some at computing device 730.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a" and "an" as used in this application are generally be construed to mean one or more unless specified otherwise or clear from context to be directed to a singular form. Also, at least one of A and B and/or the like generally means A or B and/or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A system for providing a traffic news interface, comprising:
a traffic news provider component configured to:
identify a route of a driver from a starting location to a destination location;
identify a current driver location of the driver along the route;
query traffic camera data to identify a set of traffic cameras located along the route between the current driver location and the destination location;
assign camera relevancy rankings to traffic cameras within the set of traffic cameras;
select a subset of traffic cameras from the set of traffic cameras based upon the camera relevancy rankings;
construct a traffic news interface populated with a route interface of the route and one or more traffic camera interfaces configured to display video streams associated with the subset of traffic cameras; and
display the traffic news interface through a device associated with the driver.

2. The system of claim 1, the traffic news provider component configured to:
query traffic incident data to identify a set of traffic incident reports associated with locations along the route between the current driver location and the destination location;
assign incident relevancy rankings to traffic incident reports within the set of traffic incident reports;
select a subset of traffic incident reports from the set of incident reports based upon the incident relevancy rankings; and
include the subset of traffic incident reports within the traffic news interface.

3. The system of claim 1, the traffic news provider component configured to:
query traffic condition data to identify a current traffic condition for the route;
query a map provider to obtain a map of the route;
populate the map with the route based upon the current traffic condition; and
include the map within the traffic news interface.

4. The system of claim 2, the traffic news provider component configured to:
assign at least one of a camera relevancy ranking or an incident relevancy ranking based upon a safety metric.

5. The system of claim 2, the traffic news provider component configured to:
assign at least one of a camera relevancy ranking or an incident relevancy ranking based upon a travel time sensitivity metric.

6. The system of claim 2, the traffic news provider component configured to:
assign at least one of a camera relevancy ranking or an incident relevancy ranking based upon an alternative route selection metric.

7. The system of claim 2, the traffic news provider component configured to:
evaluate vehicle telemetry of a vehicle driven by the driver to determine a driving behavior pattern; and
assign at least one of a camera relevancy ranking or an incident relevancy ranking based upon the driving behavior pattern.

8. The system of claim 2, the traffic news provider component configured to:
evaluate at least one of social network data of the driver, gaze tracking information of the driver, or driver feedback to determine a driver mood; and
assign at least one of a camera relevancy ranking or an incident relevancy ranking based upon the driver mood.

9. The system of claim 2, the traffic news provider component configured to:
assign at least one of a camera relevancy ranking or an incident relevancy ranking based upon a distance of a traffic camera or a traffic incident from the current user location.

10. The system of claim 1, the traffic news provider component configured to: populate the one or more traffic camera interfaces within a horizontal scroll interface of the traffic news interface.

11. The system of claim 2, the traffic news provider component configured to:
populate the subset of traffic incident reports within a vertical scroll interface of the traffic news interface.

12. The system of claim 1, the traffic news provider component configured to:
identify a new traffic incident;
determine an impact of the new traffic incident on a commute of the driver along the route; and
responsive to the impact of the new traffic incident exceeding a threshold, provide a push notification to the device of the new traffic incident.

13. The system of claim 1, the traffic news provider component configured to:
populate a traffic incident report interface with at least one of a delay for the driver based upon a traffic incident, a backup length caused by the traffic incident, a user that reported the traffic incident, or a description of the traffic incident.

14. The system of claim 1, the traffic news provider component configured to:
identify a new driver location of the driver;
query the traffic camera data to identify an updated set of traffic cameras based upon the new driver location;
assign new camera relevancy rankings to traffic cameras within the updated set of traffic cameras;
select an updated subset of traffic cameras from the updated set of traffic cameras based upon the new camera relevancy rankings; and
associate the one or more traffic camera interfaces with the updated subset of traffic cameras.

15. The system of claim 2, the traffic news provider component configured to:
identify a new driver location of the driver;
query the traffic incident data to identify an updated set of traffic incident reports based upon the new driver location;
assign new incident relevancy rankings to traffic incident reports within the updated set of traffic incident reports;
select an updated subset of traffic incident reports from the updated set of traffic incident reports based upon the new incident relevancy rankings; and
replace the subset of traffic incident reports within the traffic news interface with the updated subset of traffic incident reports.

16. The system of claim 2, the traffic news provider component configured to:
evaluate at least one of the subset of traffic incident reports or traffic condition data for the route to identify an alternative route; and populate the traffic news interface with the alternative route.

17. A method for providing a traffic news interface, comprising:
    identifying a route of a driver from a starting location to a destination location;
    identifying a current driver location of the driver along the route;
    querying traffic incident data to identify a set of traffic incident reports associated with locations along the route between the current driver location and the destination location;
    assigning incident relevancy rankings to traffic incident reports within the set of traffic incident reports;
    selecting a subset of traffic incident reports from the set of incident reports based upon the incident relevancy rankings;
    constructing a traffic news interface populated with a route interface of the route and the subset of traffic incident reports; and
    displaying the traffic news interface through a device associated with the driver.

18. The method of claim 17, comprising:
    querying traffic camera data to identify a set of traffic cameras located along the route between the current driver location and the destination location;
    assigning camera relevancy rankings to traffic cameras within the set of traffic cameras;
    selecting a subset of traffic cameras from the set of traffic cameras based upon the camera relevancy rankings; and
    populating the traffic news interface with one or more traffic camera interfaces configured to display video streams associated with the subset of traffic cameras.

19. The method of claim 18, comprising:
    assigning at least one of a camera relevancy ranking or an incident relevancy ranking based upon at least one of a safety metric, a time-sensitivity metric, or an alternative route selection metric.

20. A computer readable medium comprising instructions which when executed perform a method for providing a traffic news interface, comprising:
    identifying a route of a driver from a starting location to a destination location;
    identifying a current driver location of the driver along the route;
    querying traffic camera data to identify a set of traffic cameras located along the route between the current driver location and the destination location;
    assigning camera relevancy rankings to traffic cameras within the set of traffic cameras;
    selecting a subset of traffic cameras from the set of traffic cameras based upon the camera relevancy rankings;
    constructing a traffic news interface populated with a route interface of the route and one or more traffic camera interfaces configured to display video streams associated with the subset of traffic cameras; and
    displaying the traffic news interface through a device associated with the driver.

* * * * *